US00PP26640P3

(12) United States Plant Patent
Ren

(10) Patent No.: US PP26,640 P3
(45) Date of Patent: Apr. 19, 2016

(54) ***ECHINACEA* PLANT NAMED 'BALSCANDIN'**

(50) Latin Name: *Echinacea×hybrida*
Varietal Denomination: Balscandin

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 122 days.

(21) Appl. No.: 14/121,142

(22) Filed: Aug. 5, 2014

(65) Prior Publication Data

US 2016/0044851 P1 Feb. 11, 2016

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Susan McCormick Ewoldt
(74) *Attorney, Agent, or Firm* — Audrey Charles

(57) ABSTRACT

A new and distinct cultivar of *Echinacea* plant named 'Balscandin', characterized by its double-type, deep red-orange colored inflorescences, dark green-colored foliage, and moderately vigorous, compact-upright growth habit, is disclosed.

1 Drawing Sheet

Latin name of genus and species of plant claimed: *Echinacea×hybrida.*

Variety denomination: 'Balscandin'.

BACKGROUND OF THE INVENTION

The present invention relates to a new and distinct cultivar of *Echinacea* plant botanically known as *Echinacea×hybrida* and hereinafter referred to by the cultivar name 'Balscandin'.

The new cultivar originated in a controlled breeding program in Elburn, Ill. during October 2009. The objective of the breeding program was the development of *Echinacea* cultivars with a double inflorescence form and a well-branched growth habit.

The new *Echinacea* cultivar is the result of cross-pollination. The female (seed) parent of the new cultivar is the proprietary *Echinacea×hybrida* breeding selection coded E55-1, U.S. Pat. No. 7,982,110, characterized by its double-type, medium red-purple with coral colored inflorescences, dark green-colored foliage, and vigorous, upright growth habit. The male (pollen) parent of the new cultivar is the proprietary *Echinacea×hybrida* breeding selection coded E44-3-1, U.S. Pat. No. 7,982,110, characterized by its single-type, medium red-colored ray florets, dark green-colored foliage, and vigorous, semi-upright growth habit. The new cultivar was discovered and selected as a single flowering plant within the progeny of the above stated cross-pollination during July 2010 in a controlled environment in Elburn, Ill.

Asexual reproduction of the new cultivar by in vitro propagation since July 2010 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balscandin' as a new and distinct cultivar of *Echinacea* plant:

1. Double-type, deep red-orange colored inflorescences;
2. Dark green-colored foliage; and
3. Moderately vigorous, compact-upright growth habit.

Plants of the new cultivar differ from plants of the female parent primarily in inflorescence color and from plants of the male parent primarily in flower form and inflorescence color.

Of the many commercially available *Echinacea* cultivars, the most similar in comparison to the new cultivar is Double Scoop Cranberry 'Balscanery', U.S. Plant Pat. No. 24,769 and U.S. Pat. No. 7,982,110. However, in side by side comparisons, plants of the new cultivar differ from plants of 'Balscanery' in at least the following characteristics:

1. Plants of the new cultivar have an inflorescence color different from plants of 'Balscanery'; and
2. Plants of the new cultivar have darker colored foliage than plants of 'Balscanery'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balscandin'. The plants were grown in one-gallon containers for 14 weeks in a greenhouse in Elburn, Ill.

DETAILED BOTANICAL DESCRIPTION

Figure 1:
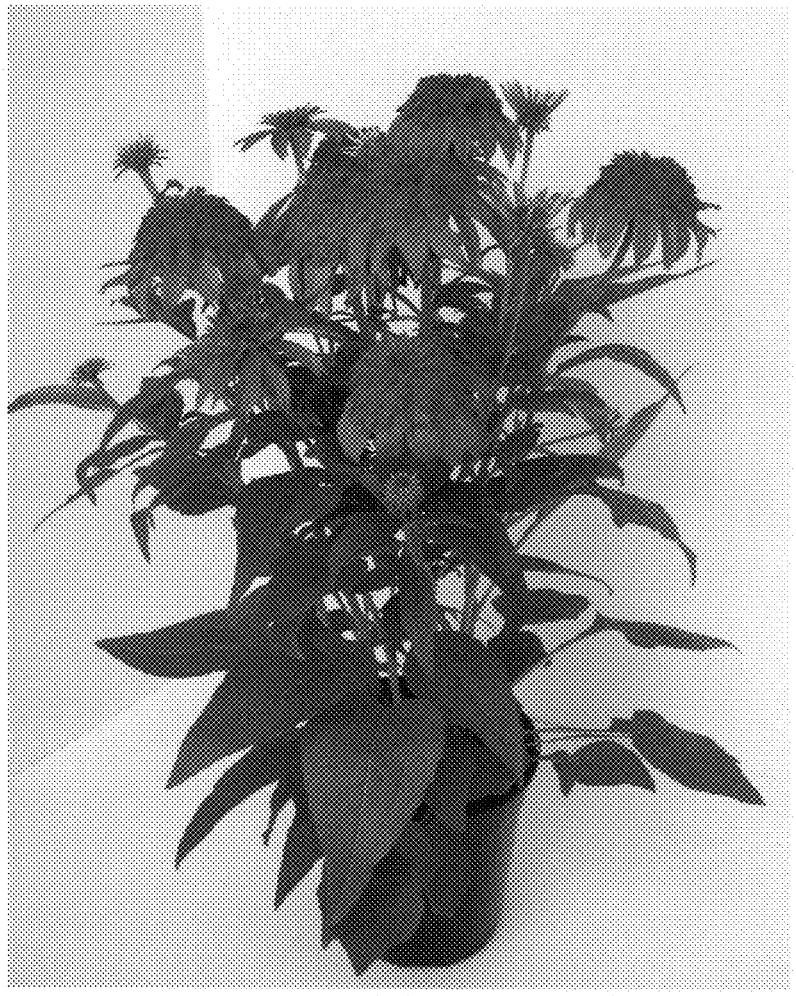
FIG. 1 illustrates a side view of the overall growth and flowering habit of 'Balscandin'.
Figure 2:
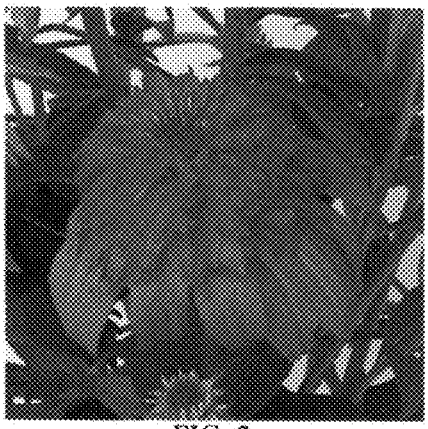
FIG. 2 illustrates a close-up view of an individual inflorescence of 'Balscandin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2014 under natural light conditions in West Chicago, Ill.

The following descriptions and measurements describe plants produced from in vitro plantlets and grown in a glass-covered greenhouse in one-gallon containers under conditions comparable to those used in commercial practice. The plants were grown in Elburn, Ill. in one-gallon containers for 14 weeks utilizing a soilless growth medium. Greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Echinacea×hybrida* cultivar Balscandin.

Parentage:

*Female parent.*—Proprietary *Echinacea×hybrida* breeding selection coded E55-1, U.S. Pat. No. 7,982,110.

*Male parent.*—Proprietary *Echinacea×hybrida* breeding selection coded E44-3-1, U.S. Pat. No. 7,982,110.

Propagation:

*Type.*—In vitro propagation is preferred, divisions are possible.

*Time to initiate roots in vitro.*—Approximately 30 days at 18° C.

*Time to produce a rooted plantlet in summer.*—Approximately 30 days at 18° C.

*Root description.*—Fine, fibrous; grey to light brown in color.

*Rooting habit.*—Moderate density, moderate branching.

Plant description:

*Commercial crop time.*—Approximately 14 to 16 weeks from a rooted tissue culture plantlet to finish in a one-gallon container.

*Growth habit and general appearance.*—Compact-upright, herbaceous perennial.

*Growth rate.*—Moderately vigorous.

*Outdoor plant performance.*—Use as bedding plants or in mixed-container plantings; at least tolerant to temperatures up to 35° C. and hardy to USDA zone 4.

*Size.*—Height from soil level to top of plant plane: Approximately 49.0 cm. Width: Approximately 49.4 cm.

*Branching habit.*—No lateral branching, flowering stems grow from base. Quantity of main stems per plant: Approximately 7.

*Stems.*—Strength: Very strong. Aspect: Nearly erect. Shape: Rounded. Length to base of inflorescence: Approximately 28.0 cm. Diameter: Approximately 6.0 mm. Length of central internode: Approximately 5.6 cm. Texture: Densely pubescent with short strigose hairs. Color of young and mature stems: 144A.

Foliage description:

*General description.*—Form: Simple. Arrangement: Alternate.

*Leaves.*—Aspect: Perpendicular to stem, subtending with age. Shape: Ovate to narrowly ovate. Margin: Entire to widely serrate. Apex: Acute. Base: Attenuate. Venation pattern: Pinnate. Length of mature leaf: Approximately 14.5 cm. Width of mature leaf: Approximately 7.0 cm. Texture of upper surface: Dull, moderately pubescent with short strigose hairs. Texture of lower surface: Moderately pubescent with short strigose hairs. Color of upper surface of young foliage: Closest to N137A with venation of 147C. Color of lower surface of young and mature foliage: Closest to 147B with venation of 145C. Color of upper surface of mature foliage: Closest to N137C with venation of 147C.

*Petiole.*—Shape: V-shaped. Length: Approximately 10.5 cm. Diameter: Approximately 3.0 mm. Texture of upper surface: Glabrous. Texture of lower surface: Glossy, sparsely covered with very short strigose hairs. Color of upper and lower surfaces: Closest to 145C.

Flowering description:

*Flowering habit.*—'Balscandin' is freely flowering under outdoor growing conditions blooming from spring through autumn and with limited flowering under short winter days in a greenhouse environment.

*Lastingness of individual inflorescence on the plant.*—Approximately 3 weeks.

Inflorescence description:

*General description.*—Type: Solitary, double, composite. Persistent. Shape: Hemispherical. Aspect: Facing upward. Arrangement: Terminal, held upright on strong peduncles. Fragrance: Faintly sweet. Quantity per plant: Approximately 9. Height: Approximately 6.0 cm. Diameter: Approximately 8.0 cm.

*Peduncle.*—Strength: Strong. Aspect: Erect to approximately 45° from vertical. Length: Approximately 15.0 cm. Diameter: Approximately 4.0 mm. Texture: Moderately pubescent with short strigose hairs. Color: 144A tinted with 187A in sun.

*Bud.*—Quantity per plant: Approximately 12. Shape: Flattened globular with immature ray florets nearly erect. Length: Approximately 1.4 cm. Diameter: Approximately 2.5 cm. Color: Outer ray florets of 154C with streaks of 64A and a bud center of 143A.

*Ray florets.*—Quantity per inflorescence: Approximately 20. Arrangement: In a single whorl, slightly imbricate. Aspect: Subtending. Shape: Narrowly elliptic. Appearance: Dull. Margin: Entire. Apex: Two to three acute tips. Base: Attenuate. Length: Approximately 4.8 cm. Width: Approximately 1.3 cm. Texture of upper and lower surfaces: Smooth, ribbed longitudinally. Color of upper surface when first open: 23A with overlay of 28A. Color of lower surface when first open: 4D with streaks of 64A. Color of upper surface when fully open: 167C with a heavy overlay of 46A, fades to 172B with age. Color of lower surface when fully open: 155D with streaks of 64A.

*Disc florets.*—Disc diameter: Approximately 6.0 cm. Quantity per inflorescence: Approximately 270. Arrangement: Spirally arranged in center of inflorescence. Shape: Tubular, free portion linear. Margin of free portion: Entire. Apex: Three acute tips. Base: Fused into a tube. Length: Approximately 2.6 cm. Length of free portion: Approximately 1.7 cm. Diameter at apex: Approximately 5.0 mm. Texture: Glabrous. Color of upper or inner surface when first open: 23A. Color of lower or outer surface when first open: 4D with streaks of 64A. Color of upper or inner surface when fully open: 167C with a heavy overlay of 46A, fades to 172B with age. Color of lower or outer surface when fully open: 155D with streaks of 64A and 145D at base.

*Receptacle.*—Shape: Conical. Height: Approximately 9.0 mm. Diameter: Approximately 1.0 cm. Color: 155D.

*Phyllaries.*—Quantity per inflorescence Approximately 55. Arrangement: In three whorls. Appearance: Dull, stiff. Shape: Narrowly ovate to lanceolate, strongly curved towards the peduncle. Margin: Entire. Apex: Acute. Base: Truncate. Length: Approximately 1.1 cm. Width: Approximately 3.0 mm. Texture of upper or inner surface: Glabrous. Texture of lower or outer surface: Surface moderately pubescent and margins densely pubescent with short strigose hairs. Color of upper surface: 137A. Color of lower surface: 137B.

*Receptacle spines.*—Number of spines per disc: Approximately 270. Shape: Acicular. Length: Approximately 1.4 cm. Width at widest point: Approximately 2.0 mm. Apex: Acute. Base: Attenuate. Texture: Glabrous. Color: Apex of 167B tipped with 187C, mid-section of 144A, and base of 145D.

*Reproductive organs.*—Vestigial.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balscandin', substantially as herein shown and described.

* * * * *